(12) United States Patent
Crawford et al.

(10) Patent No.: US 8,450,260 B2
(45) Date of Patent: May 28, 2013

(54) STRUCTURED AQUEOUS DETERGENT COMPOSITIONS

(75) Inventors: Robert John Crawford, Wirral (GB); Janet Lesley Scott, Bath (GB); Giovanni Francesco Unali, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 21 days.

(21) Appl. No.: 13/141,329

(22) PCT Filed: Dec. 24, 2009

(86) PCT No.: PCT/EP2009/067916
§ 371 (c)(1),
(2), (4) Date: Aug. 8, 2011

(87) PCT Pub. No.: WO2010/076292
PCT Pub. Date: Jul. 8, 2010

(65) Prior Publication Data
US 2011/0288000 A1    Nov. 24, 2011

(30) Foreign Application Priority Data
Dec. 29, 2008 (EP) .................. 08172985

(51) Int. Cl.
*C11D 3/223*    (2006.01)
*C11D 1/02*    (2006.01)
*C11D 1/88*    (2006.01)
*A61K 8/731*    (2006.01)
*A61Q 5/02*    (2006.01)
*A61Q 19/10*    (2006.01)

(52) U.S. Cl.
USPC .......... 510/473; 510/121; 510/127; 510/151; 510/351; 510/357; 510/426; 510/471; 510/492; 424/488; 424/70.13; 424/70.21; 424/70.22

(58) Field of Classification Search
CPC ... C11D 1/02; C11D 1/88; C11D 3/223; A61K 8/731; A61Q 5/02; A61Q 19/10
USPC .............. 510/121, 127, 151, 351, 357, 426, 510/471, 473, 492; 424/488, 70.13, 70.21, 424/70.22
See application file for complete search history.

(56) References Cited

U.S. PATENT DOCUMENTS

| | | | |
|---|---|---|---|
| 2,590,613 | A | 3/1952 | Hanson |
| 4,056,400 | A | 11/1977 | Diamantoglou |
| 5,437,810 | A | 8/1995 | Ewbank et al. |
| 6,037,460 | A | 3/2000 | Schneider et al. |
| 2005/0227902 | A1 | 10/2005 | Erazo-Majuewicz |

FOREIGN PATENT DOCUMENTS

| | | |
|---|---|---|
| DE | 837917 | 7/1951 |
| GB | 709941 | 6/1954 |
| GB | 777523 | 6/1957 |
| GB | 1299646 | 12/1972 |
| GB | 1330123 | 9/1973 |
| JP | 2006214601 | 8/2006 |
| JP | 2008001728 | 1/2008 |
| WO | WO 2009/150198 | * 12/2009 |
| WO | WO 2011/120776 | * 10/2011 |

OTHER PUBLICATIONS

International Search Report PCT/EP2009/057916, Mar. 25, 2010.

* cited by examiner

*Primary Examiner* — Brian P Mruk
(74) *Attorney, Agent, or Firm* — Michael P. Aronson

(57) ABSTRACT

A structured aqueous detergent composition comprising modified cellulose and surfactant characterized in that the composition comprises: a) 0.2 to 10 wt %, preferably 0.4 to 7 wt %, anionic surfactant or zwitterionic surfactant or mixtures thereof, b) 0.5 to 5 wt %, preferably 1 to 2 wt %, dispersed modified cellulose biopolymer, wherein the modification consists of the cellulose having its C6 primary alcohols oxidized to carboxyl moieties (acid/COOH—) on 10 to 70% of the glucose units and substantially all the remainder of the C6 positions occupied by unmodified primary alcohols, c) 0 to 10 wt % non-surfactant electrolyte; d) 0 to 15 wt % other conventional detergent composition additives e) balance water. The invention also provides a method to manufacture the composition.

15 Claims, No Drawings

STRUCTURED AQUEOUS DETERGENT COMPOSITIONS

This invention relates to structured aqueous detergent compositions comprising modified cellulose and surfactant.

BACKGROUND

Detergent compositions such as hair shampoos, hand cleansing liquids, bath foam and shower gels typically comprise one or more surfactants to provide cleaning. Such detergent compositions are often thickened to impart the desired rheology for their particular applications. A structurant may be used (either internal or external). This can impart higher levels of storage stability to the composition and it may provide it with enough structure to be able to suspend included solids or gasses, such as perfume capsules or air bubbles.

Structuring may be provided by using a higher level of surfactant than is needed for cleaning. Such surfactant containing detergent compositions, especially compositions comprising mixed surfactants, tend to be highly thixotropic, or even to gel, and this can provide the desired thickening and/or structuring. By higher levels, we mean 7 to 25 percent total surfactant when 2 to 3 percent would suffice for cleaning duty.

Many biopolymers can form reversible gels in aqueous solution. Polysaccharides, which form reversible gels and may be used as rheological additives include agar, carrageenan, furcellaran, gellan and pectin. However, though technically useful these biopolymers are more expensive than surfactants, so there is no incentive to remove surfactant and to use these materials instead. The more effective structurants may also suffer from being derived from materials, or are made using processes, that make them potentially undesirable for inclusion in a product that contacts skin and may get into the eyes.

Cellulose is a plentiful, and consequently inexpensive, biopolymer. However, in its unmodified form it is completely insoluble and cannot be dispersed into an aqueous liquid composition to achieve a stable, thickened, product.

The prior art discloses modified celluloses and their use in detergent compositions.

Complete oxidation of cellulose makes it soluble, as described in GB 1299646 and GB 1330123. Formation of polycarboxylic acids from cellulose sources is taught to be desirable in order to transform the cellulose into a detergency builder. Such modified cellulose builders require intensive processing to oxidise them sufficiently. This makes them more expensive than typical surfactants. In addition, highly oxidised cellulose tends to depolymerise and this leads to loss of structuring capability when the modified cellulose is used in aqueous systems.

In U.S. Pat. No. 5,437,810 liquid detergent compositions are viscosity modified using oxidised polysaccharide with an acid index value of 1 to 20. In its fully oxidised form, cellulose may be converted to polyglucuronic acid, which, because of its high solubility, is unsuitable as a structurant.

GB 709941 describes a process for the production of undecomposed cellulose oxidation products and the use of such products and their salts in detergent formulations. Cellulose based woody raw materials are selectively oxidised at the primary alcohol (C6) position on the anhydroglucose units. This process appears to oxidise the cellulose as much as possible. It also teaches to use low levels of the material when surfactant is present. The benefit is said to be improved detergency, presumably due to the builder effect of the oxidised cellulose. Builder materials are also taught in U.S. Pat. No. 4,056,400.

Like C6 oxidised cellulose, pectin has C6 acid groups. However, it differs from C6 partially oxidised cellulose because instead of residual primary alcohol groups it has methylated acid groups. This that makes it soluble and it therefore behaves differently in the presence of anionic or amphoteric surfactants.

Chitin can be modified to make anionic polymers by partially oxidising the primary alcohols as taught in U.S. Pat. No. 6,037,460, especially examples 7, 8, 9 and 11 where it is used to thicken a detergent composition. These chitin derivatives are very expensive and do not exhibit good structuring properties with a wide range of surfactants.

Partially and selectively oxidising cellulose at the C6 position creates cellouronates or cellouronic acids which are more water dispersible than cellulose but still relatively insoluble. Similar modified celluloses have been used in wound dressings, but for that purpose, the targeting of oxidation onto the C6 primary alcohols has not been important. C6 acids are made in the well known carboxymethyl cellulose, but this has an additional CH2 separating the acid group and the C6 carbon. Because of this, and its high degree of oxidation, CMC is soluble.

Two recent patent publications refer to C6 oxidised modified cellulose material. JP2006 241601 relates to pulp modification for paper making. Oxidation of the C6 groups to aldehydes is said to give greater wet strength to the paper. In JP2008 001728, the same inventor oxidises a variety of cellulose starting materials using the same catalytic route and then by using very high shear dispersions obtains a gel of oxidised cellulose nanofiber. No surfactant is used or added to the dispersion.

The formulator would like to have an alternative structurant for aqueous detergent compositions that is safe to use, is cheaper than the surfactant it replaces, and that can be used with a range of surfactants to allow the level of surfactant to be lowered to that required for the cleaning duty, whilst maintaining the ability to provide detergent compositions of the required rheological profile and clarity.

SUMMARY OF THE INVENTION

According to a first aspect of the present invention there is provided a structured aqueous detergent composition comprising modified cellulose and surfactant characterised in that the composition comprises:
a) 0.2 to 10 wt %, preferably 0.4 to 7 wt %, anionic surfactant or zwitterionic surfactant or mixtures thereof,
b) 0.5 to 5 wt %, preferably 1 to 2 wt %, dispersed modified cellulose biopolymer, wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols,
c) 0 to 10 wt % non-surfactant electrolyte;
d) 0 to 15 wt % other conventional detergent composition additives
e) balance water The low concentration of surfactant combined with the modified cellulose, yields soft gels with pleasing sensory characteristics. This enables the formulator to replace surfactant required for structuring (but not for cleaning) with relatively low concentrations of low cost, partially oxidised, dispersed modified cellulose.

These reduced surfactant compositions, which nonetheless maintain a thick gel-like consistency, allow suspension of sensory enhancers, such as capsules (including perfume containing encaps), beads, or glitter, which disperse rapidly in water upon dilution.

Also, according to a second aspect of the invention, there is provided a process to manufacture a structured aqueous detergent composition according to the first aspect, the process comprising the steps of:

(i) dispersing 0.5 to 5 wt % modified cellulose biopolymer in water under high shear to hydrate it, wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols,
(ii) adding 0.2 to 10 wt % of a surfactant system consisting of anionic or zwitterionic surfactant, or mixtures of such surfactants, to this aqueous dispersion,
(iii) optionally also adding 0 to 10 wt % non-surfactant electrolyte consisting of low molecular weight salt, and
(iv) optionally mixing in up to 15 wt % 0 to 15 wt % other conventional detergent composition additives to make a structured aqueous detergent composition.

The modified cellulose biopolymer (i) is a water insoluble, water dispersible modified cellulose in which only a proportion of its C6 primary alcohol groups have been oxidised to acid groups. Cellulose where all such alcohols have been oxidised is called polyuronic acid or polyglucuronic acid. Such fully oxidised material is soluble in water. It is unsuitable for use in the present invention for two reasons. Firstly, the cost of the extra processing required to create more than 70% substitution of primary alcohols by carboxylic acid groups makes it not cost effective as a replacement for surfactant and second the highly oxidised material tends to include unwanted depolymerised cellulose, which leads to a reduction of yield of insoluble dispersible structurant.

In this specification, a modified cellulose biopolymer is said to be water soluble, if it leaves less than 10 wt % of its dry mass as undissolved residue when a 2 g dry sample is added to 1 litre of agitated demineralised water at 25° C.

Totally unoxidized (unmodified) cellulose is unable to function as a structurant. Oxidising the cellulose to have at least 10% of the primary alcohols converted to carboxylic acids makes the cellulose dispersible in water and when mixed within the surfactant system the resulting structured liquid or gel maintains the cellulose in a dispersed state so it does not settle over time.

Once the high shear dispersion of the modified cellulose has taken place, the remaining process steps can take place in a conventional stirred tank, at relatively low shear. This allows the formulator to make a stock of aqueous dispersion of the modified cellulose, preferably stabilised by the further addition of anionic or amphoteric surfactants or mixtures thereof and possibly also stabilised by the addition of some non-surfactant electrolyte, such as sodium chloride. Further ingredients of a detergent composition can be added to this mixture when needed to enable easy late-stage variations in composition before products are packaged.

The structured aqueous detergent compositions also have the desired advantage that lower levels of surfactants can be used and that some co-surfactant could be omitted entirely to simplify the formulation. It is also possible that surfactants or surfactant combinations previously regarded as unsuitable for use in hand applied compositions, like hair detergents, may now be suitable, due to their amounts being reduced.

The invention provides structured aqueous detergent compositions having a structurant derived from entirely renewable, non-petrochemical resources; structured aqueous detergent compositions having a reduction in surfactant with retention of structuring; structured aqueous detergent compositions having pleasant sensory characteristics; structured aqueous compositions capable of suspending visual and sensory particles stably for at least as long as typical storage durations, and a biodegradable product at end of use.

DETAILED DESCRIPTION OF THE INVENTION

The Cellulose Starting Material

Several factors influence the choice of a suitable starting material.

More porous unmodified cellulosic material will oxidise more rapidly. Characterisation of surface area or porosity is readily achieved by porosimetry or BET measurements. In general, those starting materials that oxidise more rapidly due to their low crystallinity and higher surface area and/or porosity, prove easier to disperse than those that oxidise less rapidly.

The rate of oxidation is also affected by the dimensions of the particles of cellulose starting material; the reduction in rate for longer (>500 micron) fibres is significant. Fibres less than 500 microns long are therefore preferred for this reason and due to the added difficulty in agitation of the longer fibres. While oxidation results in significant gross particle size reduction, this does not compensate for decreased fibril surface accessibility in the long fibres.

Celluloses that have not been previously subjected to acid hydrolysis are a preferred starting material, due to reactivity, cost and resultant product dispersibility.

Relatively unrefined α-cellulose, for example filter aid fibres, provides one of the most readily oxidised and dispersed sources of cellulose. An unexpected advantage of the process of the invention is the ability to use unbleached starting materials that might be regarded as unsuitable for structuring a clear liquid detergent composition. This is because the oxidation process also serves to bleach coloured components, such as lignin, in such unbleached cellulose starting materials.

Oxidation

Because of its known specificity for primary alcohol oxidation TEMPO (and related nitroxy radical species) mediated oxidation of cellulose is preferred. The process proceeds well without cooling, at relatively high weight % cellulose in the initial suspension. Simple workup procedures afford clean material suitable for dispersion. Such TEMPO mediated oxidation of cellulose is described in the published literature and the skilled worker will be able as a matter of routine to adapt known methods to achieve the oxidation required by this invention.

While aqueous NaOCl/TEMPO/NaBr is a highly preferred oxidation system. There are a number of other systems available to the skilled worker, especially for large scale production. Among such systems, there may be mentioned use of peracetic acid or monoperoxysulfate salts (Oxone®) as the oxidant with 4-acetamido-2,2,6,6-tetramethylpiperidine-1-oxyl (4-acetamido-TEMPO) as the radical transfer catalyst or mediator and sodium bromide co-catalyst for the oxidation. Elimination of chlorine from the oxidation system is environmentally desirable.

The use of 4-acetamido-TEMPO as radical transfer catalyst is also advantageous as, although it has a higher molecular weight than TEMPO, it has significantly lower vapour pressure reducing potential exposure hazards. Many other 4-substituted TEMPO analogues exist, but many, such as 4-hydroxy-TEMPO exhibit poor stability. TEMPO on solid supports or on soluble polymers may be used.

Electrochemical oxidation is a potentially clean means of effecting oxidation of carbohydrate moieties, although mediation by a radical transfer catalyst (such as TEMPO) is still required.

Laccase mediated oxidation, which also requires a radical transfer catalyst (e.g. TEMPO) but replaces the oxidant with an enzyme, may advantageously be used.

Using the TEMPO system the degree of reproducibility of oxidation of cellulose from the same source is good.

Degree of Oxidation

Throughout this specification when we refer to the degree of oxidisation of the modified cellulose we refer to the percentage glucose units oxidised to carboxylic acid as measured by titration with sodium hydroxide. It is assumed that all oxidation takes place at the primary alcohol positions. A reasonable assumption, given that primary alcohol specific oxidation chemistry is employed. Furthermore it is assumed that all oxidation leads to carboxylic acid formation.

Degree of polymerisation (DP) does not seem greatly to influence the performance of the modified cellulose. The key thing is that the modified cellulose must remain insoluble. During oxidation, there is some degradation of the cellulose allowing release of polymer chains. It is particularly advantageous to keep this to a minimum in order to increase the yield of the modified insoluble cellulose material suitable for structuring applications. We have determined that above 70% oxidisation, the yield is unacceptably low and the processing costs become unacceptably high.

The degree of oxidation of the modified cellulose should lie in the range 10 to 70%. As the degree of oxidation increases, the amount of soluble material produced will rise and this reduces the yield of insoluble structuring material, thus the higher degrees of oxidation confer no real structuring benefits. For this reason, it is preferred to restrict the degree of oxidation to 60%, or even 50% and the most preferred modified materials have degrees of oxidation even lower than 40 or sometimes even lower than 30%.

To achieve a high enough dispersibility/solubility for the modified cellulose to act as a structurant it must be oxidised to at least 10%. The exact amount of oxidation required for a minimum effect will vary according to the starting material used. Preferably, it is at least 15% oxidised and most preferably, at least 20% oxidised.

Dispersal of the Modified Cellulose,

At small scale, high energy sonication is the preferred method to give the high shear necessary to achieve the aqueous dispersion of the modified cellulose. However, other techniques are more suitable for large scale applications. These include the use of a high speed and high shear stirrer, or a blender, or a homogeniser. Homogenisation may achieve higher levels of dispersed material than are attainable via sonication.

When degrees of oxidation of less than 10% are used, the partially oxidised cellulose proves too resistant to dispersion to produce a transparent or translucent mixture and higher energy input is required. Provided the lower limit of 10% is exceeded, those modified celluloses with a lesser degree of oxidation appear to provide greater structuring capacity once dispersed. This is attributed to less degradation of the material during oxidation and thus the existence of longer individual dispersed (not dissolved) fibrils. This may be because the structure of the cellulose starting material is partially retained, but the fibrils are rendered dispersible by the introduction of negatively charged functional groups on the surface during oxidation.

Oxidised, dispersed cellulose is a largely insoluble polymer that occurs in the form of well dispersed fibrils rather than isolated solvated polymer chains. The fibrils have a large aspect ratio and are thin enough to provide almost transparent dispersions. Carboxylate groups provide anionic surface charge, which results in a degree of repulsion between fibrils, militating against their reassociation into larger structures. Addition of acid to dispersions of oxidised cellulose results in separation of gelled material while at pH between ca 5-9 fibrils may be maintained in a dispersed form as the COO— salt of an appropriate counterion.

The Surfactants

The total amount of surfactant (including any co-surfactant, and/or any emulsifier) in the detergent compositions is from 0.2 to 10 wt %, preferably from 0.4 to 7 wt %, more preferably from 0.5 to 5% by total weight surfactant based on the total weight of the composition.

Anionic Surfactants

Although any of the anionic surfactants conventionally used or usable in personal care (skin contact) compositions may be used, either alone or in combination, it is preferable that surfactants having mildness to the skin and especially naturally derived and processed surfactants are used at least for part of the total surfactant system.

Preferred anionic surfactants include sodium lauroyl sarcosinate, sodium lauroyl lactylate, sodium cocoyl glutamate, disodium alkylpolyglucose sulfosuccinate/citrate, sodium lauryl ether sulphate (1-3 EO).

Other examples of suitable anionic surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical types of anionic surfactants for use in detergent compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic surfactants of these types are sodium lauryl sulphate, sodium lauryl ether sulphate(n)EO, (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid (n) EO (where n is from 10 to 20).

Mixtures of any of the foregoing anionic surfactants may also be used.

The total amount of anionic surfactant in detergent compositions of the invention generally ranges from 0.1 to 10%, preferably from 0.5 to 7%, more preferably from 1 to 5% by total weight anionic surfactant based on the total weight of the composition.

Amphoteric Surfactants

Although any of the amphoteric surfactants conventionally used or usable in personal care (skin contact) compositions may be used, either alone or in combination, it is preferable that surfactants having mildness to the skin and especially naturally derived and processed surfactants are used at least for part of the total surfactant system. Thus, a preferred surfactant could be olivamidopropyl betaine, a natural analogue of CAPB derived from olive feed stock. A preferred amphoteric surfactant is sodium cocoamphoacetate. Amphoteric surfactants are also called zwitterionic surfactants.

Other examples of amphoteric surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric surfactants for use in detergent compositions include lauryl amine oxide, cocodimethyl sulphopropyl betaine, lauryl betaine, cocamidopropyl betaine and sodium cocoamphoacetate. A preferred amphoteric surfactant is cocamidopropyl betaine.

Mixtures of any of the foregoing amphoteric surfactants may also be suitable. The total amount of amphoteric surfactant in detergent compositions of the invention generally ranges from 0.1 to 10%, preferably from 0.5 to 7%, more preferably from 1 to 5% by total weight anionic surfactant based on the total weight of the composition.

Mixtures of anionic and amphoteric surfactants may be used, especially when it is desired to combine the cleaning effect of the anionic surfactant with the foaming power of the amphoteric surfactant.

Other Surfactants

Nonionic surfactants may optionally be used as co-surfactants, together with the essential anionic or amphoteric surfactants. Suitable nonionic surfactants include biosurfactants, for example Sopholiance S, an amphiphilic sophorolipid biosurfactant. Another type of suitable nonionic co-surfactant is sorbitan trioleate.

For example, representative nonionic surfactants that can be included in detergent compositions of the invention include condensation products of aliphatic (C8-C18) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamine.

Further nonionic surfactants, which can be included in detergent compositions of the invention, are the alkyl polyglycosides (APGs). Typically, the APG is one which comprises an alkyl group connected (optionally via a bridging group) to a block of one or more glycosyl groups. Preferred APGs are defined by the following formula:

RO-(G)$_n$ wherein R is a branched or straight chain alkyl group, which may be saturated or unsaturated, and G is a saccharide group.

R may represent a mean alkyl chain length of from about C5 to about C20. Preferably, R represents a mean alkyl chain length of from about C8 to about C12. Most preferably, the value of R lies between about 9.5 and about 10.5. G may be selected from C5 or C6 monosaccharide residues, and is preferably a glucoside. G may be selected from the group comprising glucose, xylose, lactose, fructose, mannose and derivatives thereof. Preferably, G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as Oramix NS10 ex Seppic; Plantaren 1200 and Plantaren 2000 ex Henkel.

Other sugar-derived nonionic surfactants which can be included in compositions of the invention include the C10-C18 N-alkyl (C1—C6) polyhydroxy fatty acid amides, such as the C12-C18 N-methyl glucamides, as described for example in WO 92 06154 and U.S. Pat. No. 5,194,639, and the N-alkoxy polyhydroxy fatty acid amides, such as C10-C18 N-(3-methoxypropyl) glucamide.

It is preferred to avoid use of cationic surfactants due to their charge being the opposite of that of the modified cellulose. This causes unwanted interactions and precipitation to occur.

Optional Non-Surfactant Electrolyte

The non-surfactant electrolyte is optional; in combination with surfactant it does not thicken as much as would be expected. This is not fully understood. The preferred non-surfactant electrolyte is a water soluble inorganic or organic salt with a molecular weight of less than 500. The electrolyte preferably has a monovalent cation, however at low (less than 2 wt %) levels salts with divalent cations, such as Calcium Chloride, may be used.

Sodium Chloride is the preferred non-surfactant electrolyte.

Other Conventional Additives

Apart from a general need to avoid use of cationic polymers, that cause precipitation with the anionic charged surfactants over a wide range of pH as used in personal care products, all of the usual additives found in personal product compositions may be added to the aqueous structured compositions comprising the surfactant and modified cellulose according to the invention. The total amount of such additives will not normally exceed 15 wt %. The balance of the composition is water.

The detergent compositions may comprise a second suspending agent of the type conventionally employed. The detergent compositions may comprise hair and/or skin conditioning agents.

Adding small amounts of perfume does not destabilise the structured aqueous detergent compositions. Furthermore, perfume encapsulates, small beads, free emulsions and even air bubbles stay suspended when dispersed at low shear in the structured aqueous detergent compositions.

If too much water is added to the composition there is an eventual loss of structuring, but provided the concentration of modified cellulose structurant and surfactant system is kept above the lower limits of the invention the structuring is maintained. Advantageously it is kept above a preferred lower limit of 1 wt % for each of the structurant and the surfactant system.

The detergent compositions may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

The invention will now be further described, with reference to the following non-limiting examples.

Exemplary Method for Production of Modified Cellulose

The cellulose is suspended in water; the NaBr is added as a 0.5 M aqueous solution. TEMPO catalyst is then added as a slightly acidified 0.03 M aqueous solution. Then add NaOCl solution (assay 5-6.5%) with the quantity of water adjusted to compensate for the differing NaOCl quantities i.e. volume.

Adjust to pH 10.5, maintain at this pH by addition of NaOH during reaction under stirring at room temperature (nominally 25° C.).

Adjust pH to about 6 and isolate the modified cellulose by centrifuging. Wash with water and recentrifuge. Finally, the pH may be adjusted to neutral using NaOH.

Modified Celluloses #1 to #8

A number of samples of modified cellulose with differing degrees of oxidation were prepared following the exemplary method. The starting material used was α-cellulose, C8002 from Sigma Aldrich. Approx. 5 g was used for each sample. Details are summarized in Table 1.

TABLE 1

Modified cellulose samples with different % oxidation

|  | Dry mass cellulose/g | Mole ratio catalysts/ reagent relative to glucose units | | | Degree of oxidation = % glucose units oxidised, based on titration with NaOH |
|---|---|---|---|---|---|
|  |  | TEMPO | NaBr | NaOCl | % |
| #1 | 4.85 | 0.0075 | 0.16 | 1.36 | 71 |
| #2 | 4.75 | 0.0077 | 0.17 | 1.26 | 68 |
| #3 | 4.81 | 0.0075 | 0.16 | 1.12 | 59 |
| #4 | 4.77 | 0.0076 | 0.17 | 1.01 | 53 |
| #5 | 4.80 | 0.0076 | 0.16 | 0.87 | 46 |
| #6 | 4.75 | 0.0077 | 0.17 | 0.76 | 38 |
| #7 | 4.83 | 0.0075 | 0.16 | 0.62 | 31 |
| #8 | 4.87 | 0.0075 | 0.16 | 0.49 | 25 |

All eight samples were able to be dispersed in water by sonication for up to 40 minutes. Those less oxidised gave somewhat turbid suspensions. The more highly oxidised samples became completely transparent after a relatively short sonication time.

Aqueous dispersions of up to 2% (by weight) of modified cellulose are free-flowing (although more viscous than water). Above this concentration, or in the presence of electrolytes, the dispersions become thicker, eventually forming gels, which may be opaque.

Example 1

Adding Surfactant

Surfactants were added to sonicated dispersions of modified cellulose samples with differing degrees of oxidation. No extra electrolyte was added. Surprisingly, addition of small quantities of surfactant to the dispersions yielded clear gels. Amounts of surfactant given in the table are based on active content. The activity of the nonionic surfactant was not certain, but is thought to be near to 100%. Surfactants used were as follows:

|  |  |  | % active |
|---|---|---|---|
| Anionic surfactants | | | |
| LS | Sodium lauroyl sarcosinate | Medialan LD | 31 |
| LL | Sodium lauroyl lactylate | Pationic 138C | 98 |
| CG | Sodium cocoyl glutamate | Hostapon KCG | 25 |
| PGS | Disodium coco-glucoside sulfosuccinate | Eucarol AGE/SS | 45 |
| PGC | Disodium coco-glucoside citrate | Eucarol AGE/EC | 31 |
| SLES1 | Sodium lauryl ether sulphate (1 EO) | | 70 |
| SLES3 | Sodium lauryl ether sulphate (3 EO) | | 70 |
| Amphoteric surfactant | | | |
| CAA | Sodium cocoamphoacetate | Miranol Ultra C32 | 31 |
| Nonionic surfactant | | | |
| STO | sorbitan trioleate | Span 85V Pharma | ≦100 |

Results are given in Table 2.

TABLE 2

Surfactant/modified oxidised cellulose compositions

Modified cellulose biopolymer = 30% oxidised

| | Example | | | | | | |
|---|---|---|---|---|---|---|---|
| | 1.1 | 1.2 | 1.3 | 1.4 | 1.5 | 1.6 | 1.7 |
| Cell % | 1.3 | 1.3 | 1.3 | 1.3 | 1.3 | 1.3 | 1.3 |
| Surfactant % | 0.25 | 0.28 | ≦0.9 | 0.45 | 0.2 | 0.39 | — |
| Surfactant | CAA | PGC | STO | PGS | CG | LL | — |
| Surfactant Type | Amphoteric | Anionic | Nonionic | Anionic | Anionic | Anionic | None |
| | Thixotropic gel Medium Bubbles trapped Translucent | Thixotropic gel Soft No bubbles Translucent | Free-flowing liquid Opaque | Thixotropic gel Medium Bubbles trapped Translucent | Thixotropic gel Lumpy Semi-translucent | Thixotropic gel Medium - evidence of particles Semi-translucent | Thickened liquid Almost clear |

Modified cellulose biopolymer = 43% oxidised)

| | Example | | | | | | |
|---|---|---|---|---|---|---|---|
| | 1.8 | 1.9 | 1.10 | 1.11 | 1.12 | 1.13 | 1.14 |
| Cell/% | 1.3 | 1.3 | 1.3 | 1.3 | 1.3 | 1.3 | 1.3 |
| Surfactant % | 0.62 | 0.65 | 0.65 | 1.17 | 0.35 | 0.88 | — |

TABLE 2-continued

| Surfactant/modified oxidised cellulose compositions | | | | | | | |
|---|---|---|---|---|---|---|---|
| Surfactant | CAA | PGC | LS | PGS | CG | LL | — |
| Surfactant Type | Amphoteric | Anionic | Anionic | Anionic | Anionic | Anionic | None |
| | Thixotropic gel Clear gel Firm Traps bubbles for months Some syneresis | Thixotropic gel Clear gel medium Traps bubbles for months | Thixotropic gel Clear gel medium Traps bubbles for months | Thixotropic gel Clear gel Firm Traps bubbles for months Breaks up on shaking/ some syneresis | Thixotropic gel clear-gel medium Traps bubbles for months Breaks up on shaking/ some syneresis | Thixotropic gel Semi-translucent gel traps bubbles Breaks up on shaking/ evidence of gel particles | Thickened liquid |

Examples 1.3, 1.7 and 1.14 are comparative, as they do not include any anionic or amphoteric surfactant. Table 2 shows that combination of oxidised, dispersed cellulose with anionic surfactants and zwitterionic (betaine) surfactants provides gelled material, while no such gels result in the presence of the nonionic sorbitan surfactant.

Examples 2 and 3

Surfactant and Electrolyte Concentration

A series of experiments were carried out in which concentrations of NaCl electrolyte and two anionic surfactants (SLES 1EO and SLES 3EO) were altered. Water, oxidised cellulose dispersion, surfactant solution, and NaCl solution, were added in that order. The degree of oxidation of the modified cellulose was 28-29% for all these samples. Finally, pH was adjusted with $HCl_{(aq)}$ and total volume made up with water. The concentration of oxidised dispersed cellulose was varied between 0.5 and 1.5 wt %; the concentration of NaCl between 0 and 2 wt % and that of the surfactant between 0 and 10 wt %. Results for these surfactants are summarized in Tables 3, and 4. SLES 1EO (as used in detergent formulations); NaCl; pH adjusted to 6 is shown in Table 3. SLES 3EO (as used in concentrated laundry); NaCl pH adjusted to 8 is shown in Table 4. Comparative examples are indicated using N+letter. Examples of inventive compositions are indicated by N+number.

TABLE 3

| Example 2 SLES1 | | | | | | | | | | | | |
|---|---|---|---|---|---|---|---|---|---|---|---|---|
| No surfactant/variable oxidised cellulose and NaCl content | | | | | | | | | | | | |
| | Example | | | | | | | | | | | |
| | 2A | 2B | 2C | 2D | 2E | 2F | 2G | 2H | 2J | 2K | 2L | 2M |
| Mod cell/% | 0.5 | 1.0 | 1.5 | 0.5 | 1.0 | 1.5 | 0.5 | 1.0 | 1.5 | 0.5 | 1.0 | 1.5 |
| NaCl/% | 0.0 | 0.0 | 0.0 | 0.2 | 0.2 | 0.2 | 1.0 | 1.0 | 1.0 | 2.0 | 2.0 | 2.0 |
| Surfact./% | 0.0 | 0.0 | 0.0 | 0.0 | 0.0 | 0.0 | 0.0 | 0.0 | 0.0 | 0.0 | 0.0 | 0.0 |
| | Free flow-ing - water-like | Free flow-ing - water-like | Free flow-ing | Free flow-ing; some solid (little) | Free flow-ing; some solid (little) | Free flow-ing - some thick-ening | Free flow-ing - some thick-ening | Single mass medium/ soft gel | Firm mass of gel - shows syner-esis | Single mass - soft gel (some liquid?) | Single mass med-ium gel | Gelled mass of par-ticles |

| No NaCl/variable oxidised cellulose and surfactant content | | | | | | | | |
|---|---|---|---|---|---|---|---|---|
| | Example | | | | | | | |
| | 2.1 | 2.2 | 2.3 | 2.4 | 2.5 | 2.6 | 2.7 | 2.8 |
| Mod cell/% | 0.5 | 1.0 | 1.5 | 0.5 | 1.0 | 1.5 | 0.5 | 1.0 |
| NaCl/% | 0.0 | 0.0 | 0.0 | 0.0 | 0.0 | 0.0 | 0.0 | 0.0 |
| Surfact/% | 2.5 | 2.5 | 2.5 | 5.0 | 5.0 | 5.0 | 10.0 | 10.0 |
| | Free-flowing liquid | Free-flowing liquid - small quant gel sep | Free-flowing liquid some thickening | Free-flowing liquid | Gelled mass - soft - flows | Gelled mass - firm - exhibits syneresis | Single mass soft gel* | Gel particles tending to form mass |

TABLE 3-continued

Example 2 SLES1

Variable NaCl, surfactant and oxidised cellulose content

| | Example | | | | | | | | |
|---|---|---|---|---|---|---|---|---|---|
| | 2.9 | 2.10 | 2.11 | 2.12 | 2.13 | 2.14 | 2.15 | 2.16 | 2.17 |
| Mod cell/% | 1.0 | 1.0 | 1.0 | 1.0 | 1.0 | 1.0 | 1.0 | 1.0 | 1.0 |
| NaCl/% | 0.2 | 1.0 | 2.0 | 0.2 | 1.0 | 2.0 | 0.2 | 1.0 | 2.0 |
| Surfact/% | 2.5 | 2.5 | 2.5 | 5.0 | 5.0 | 5.0 | 10.0 | 10.0 | 10.0 |
| | Single mass soft gel | Gel particles tending to form mass - free flowing | Gel particles tending to form mass - free flowing | Gel particles tending to form mass - free flowing | Gel particles form mass - float when aerated | Gel particles - free flowing | Gel particles form mass - float when aerated | Gel particles - form flowing | Gel mass - pours slowly |

*breaks up on shaking

SLES 1 EO is known to form gels, at relatively low concentrations, in the presence of electrolytes such as NaCl, but the observed similar behaviour with other surfactants, for example as described in example 3 below, implies that the effect is due to an interaction of the oxidised cellulose with the surfactant electrolytes.

TABLE 4

Example 3 SLES 3EO

| | Example | | |
|---|---|---|---|
| | 3A | 3B | 3C |
| Mod cell/% | 1.0 | 1.0 | 1.0 |
| NaCl/% | 0.2 | 1.0 | 2.0 |
| Surfact/% | 0.0 | 0.0 | 0.0 |
| | Discarded - error in delivery V | Single mass medium/soft gel | Single mass medium gel - tends to |

| | Example | | |
|---|---|---|---|
| | 3.1 | 3.2 | 3.3 |
| Mod cell/% | 1.0 | 1.0 | 1.0 |
| NaCl/% | 0.0 | 0.0 | 0.0 |
| Surfact/% | 2.5 | 5.0 | 10.0 |
| | Free-flowing liq - v. slightly thickener | Gel particles tend to form mass** | Gel particles tend to form firm mass** |

| | Example | | | | | | | |
|---|---|---|---|---|---|---|---|---|
| | 3.4 | 3.5 | 3.6 | 3.7 | 3.8 | 3.9 | 3.10 | 3.11 |
| Mod cell/% | 1.0 | 1.0 | 1.0 | 1.0 | 1.0 | 1.0 | 1.0 | 1.0 |
| NaCl/% | 0.2 | 1.0 | 2.0 | 0.2 | 1.0 | 2.0 | 0.2 | 1.0 |
| Surfact/% | 2.5 | 2.5 | 2.5 | 5.0 | 5.0 | 5.0 | 10.0 | 10.0 |
| | Single mass soft gel - flows on shaking | Single mass medium/ firm gel | Gel particles - free- flowing | Gel particles tending to form single mass** | Gel particles form mass but break up easily | Gel particles free- flowing but thick | Gel particles tending to form mass | Gel particles tending to form mass (trap air bubbles) |

For each surfactant, combinations exist that provide product of soft gel-like consistency which may be induced to flow by the application of shear stress and which resets on standing. Addition of high concentrations of surfactant and salt leads to the formation of gel particles, which may separate, floating or sinking, depending on the inclusion of air bubbles. The gel formed by addition of NaCl alone appeared opalescent, while those with the same quantity of NaCl and the anionic surfactants were clear.

Example 4

Other Additives

A series of samples were made, in which the modified cellulose and surfactant aqueous compositions were combined with other formulation ingredients.

A combination of SLES 1 EO (5% by wt) and dispersed oxidised cellulose (1.3% by wt) yields a soft transparent gel, which, on shaking, breaks up and flows, regelling on standing post disruption. Bubbles, solid beads, encaps or other visual aids added to the suspension and dispersed by shaking remain suspended in the transparent gel. Perfumed microcaps and the associated bubbles, formed on shaking, remain suspended for several months Similarly, beads or encapsulated benefit agents and glitter particles remain homogeneously suspended for several months.

Beads, bubbles and glitter particles were suspended in vials containing ca 2 mL of a soft gel formed by addition of SLES 1EO to a dispersion of oxidised cellulose (composition: 1.3% oxidised cellulose; 5% SLES 1EO). a) plus 114 mg perfume microcapsule suspension; b) 86 mg perfume microcaps suspension c) plus 125 mg perfume microcaps d) plus 17 mg "Colorona" Glitter Copper powder. Shaking of the loaded gels renders them flowable and regelling occurs reasonably rapidly post disturbance. Gels are smooth to the touch with no feeling of "graininess", spread easily on the skin and may be extruded smoothly through an orifice or pumped.

Addition of hydrophobic oils such as liquid paraffin or silicon oil DC200, 50 cS viscosity (20%) to mixtures of dispersed oxidised cellulose (0.9%) and SLES 1EO (5.7%) followed by homogenisation using a handheld Ultraturrax device, leads to the formation of white emulsions. Addition of a small amount of NaCl converts the silicon oil emulsion to a firm gel. (By comparison, a mixture of silicon oil, water and SLES in similar ratios rapidly separates yielding a clear aqueous solution topped by the creamed emulsified oil).

The invention claimed is:

1. A structured aqueous detergent composition comprising modified cellulose and surfactant characterised in that the composition comprises:
   a) 0.2 to 10 wt % anionic surfactant or zwitterionic surfactant or mixtures thereof,
   b) 0.5 to 5 wt % dispersed modified cellulose biopolymer, wherein the modification consists of the cellulose having its C6 primary alcohols oxidised to carboxyl moieties (acid/COOH—) on 10 to 70% of the glucose units and the remainder of the C6 positions occupied by unmodified primary alcohols, and wherein all oxidation takes place at the primary alcohol position;
   c) 0 to 10 wt % non-surfactant electrolyte;
   d) 0 to 15 wt % other conventional detergent composition additives
   e) balance water.

2. A composition according to claim 1 further comprising perfume, perfume encapsulates, small beads, free emulsions air bubbles and combinations thereof suspended in the composition.

3. A composition according to claim 1 having more than 1 wt % modified biopolymer structurant and more than 1 wt % surfactant system.

4. A composition according to claim 1 in which the degree of oxidation is less than 50%.

5. A composition according to claim 1 in which the modified cellulose is oxidised to at least 20%.

6. A composition according to claim 1 in which the total amount of surfactant, including any co-surfactant, and/or any emulsifier, in the detergent compositions is from 0.4 to 7 wt %.

7. A composition according to claim 1 comprising an anionic surfactant selected from the group comprising sodium lauroyl sarcosinate, sodium lauroyl lactylate, sodium cocoyl glutamate, disodium polyglucose sulfosuccinate/citrate, sodium lauryl ether sulphate (1-3 EO).

8. A composition according to claim 1 comprising an amphoteric surfactant which is sodium cocoamphoacetate.

9. A composition according to claim 1 in which the non-surfactant electrolyte is sodium chloride in an amount of from 1 to 10 wt %.

10. A composition according to claim 1 in which the other additives are included in amount of up to 15 wt % for enhancing performance and/or consumer acceptability the other additives being selected from fragrance, dyes and pigments, pH adjusting agents, pearlescers or opacifiers, viscosity modifiers, preservatives, natural hair nutrients, fruit extracts, sugar derivatives and amino acids.

11. A process to manufacture a structured aqueous detergent composition according to claim 1, the process comprising the steps of:
   dispersing 0.5 to 5 wt % modified cellulose biopolymer in water under high shear to hydrate it, wherein the modification consists of the cellulose having its C6 primary alcohols oxidised to carboxyl moieties (acid/COOH—) on 10 to 70% of the glucose units and the remainder of the C6 positions occupied by unmodified primary alcohols and wherein all oxidation takes place at the primary, alcohol position,
   (ii) adding 0.2 to 10 wt % of a surfactant system consisting of anionic or zwitterionic surfactant, or mixtures of such surfactan to this aqueous dispersion,
   (iii) optionally also adding 0 to wt % ion-surfactant electrolyte,
   (iv) optionally mixing in up to 15 wt % other conventional detergent additives to make a structured aqueous detergent composition.

12. A process according to claim 11 in which the oxidation is catalysed using TEMPO.

13. A process according to claim 11 in which the non surfactant electrolyte has a monovalent cation.

14. The composition according to claim 1 wherein the dispersed modified cellulose biopolymer is present in the composition at from 1 to 2 wt %.

15. The composition according to claim 1 wherein the modified cellulose biopolymer is made from an unbleached a cellulose.

* * * * *